United States Patent [19]
Brittain

[11] Patent Number: 5,969,098
[45] Date of Patent: Oct. 19, 1999

[54] YEAST-TOXIN-RELATED PROTEIN FOR ANTIMICROBIAL VACCINE AND STERILIZING PRESERVATIVE USE

[75] Inventor: Andrew Marsh Brittain, Huntsville, Ala.

[73] Assignee: CyberChemics, Inc., Huntsville, Ala.

[21] Appl. No.: 08/898,885

[22] Filed: Jun. 6, 1997

[51] Int. Cl.[6] .............................. A61K 38/10; C07K 7/08; C07K 14/39
[52] U.S. Cl. .............................. 530/326; 514/13; 514/14; 530/327; 530/824
[58] Field of Search .............................. 514/2, 8, 12, 13, 514/14; 530/300, 322, 324, 325, 326, 327, 350, 395, 824

[56] References Cited

U.S. PATENT DOCUMENTS 5,294,605  3/1994  Houghten et al. .......................... 514/13

OTHER PUBLICATIONS

Sor et al. Structure of a linear plasmid of the yeast . . . Current Genetics. vol. 9, pp. 147–155, 1985.

Sugisaki et al. kluyveromyces lactis killer toxin . . . Nature. vol. 304, pp. 464–466, Aug. 4, 1983.

*Primary Examiner*—Jeffrey E. Russel
*Attorney, Agent, or Firm*—Leo G. Lenna, Esq.; Bryan Cave LLP

[57] ABSTRACT

The invention is directed to compounds having the following sequences: Leu Val Leu Leu Lys Lys Leu Met Lys Lys Tyr Lys Lys Leu Lys Lys Leu Gly Gly Leu as set forth in SEQ. ID. No. 1; Leu Leu Leu Leu Lys Leu Leu Leu Lys Lys Asn Pro Lys Leu Lys Lys Leu Ile Gly Val as set forth in SEQ. ID. No. 2; Leu Leu Leu Leu Lys Lys Leu Leu Lys Leu Met Asn Leu Leu Lys Lys Leu Gly His Tyr as set forth in SEQ. ID. No. 3; and Lys Lys Ile Lys Glu Lys Tyr Asp Lys Met Lys Lys as set forth in SEQ. ID. No. 4.

4 Claims, 4 Drawing Sheets

| ANTIMICROBIAL DATA | | ORGANISM (ATCC) | SEQ. ID | 1 | 2 | 3 |
|---|---|---|---|---|---|---|
| | GRAM NEGATIVE BACTERIA | E. COLI (25922) | | 16.00 | 32.00 | 8.00 |
| | | PS. ARUGINOSA (13883) | | 8.00 | 125.00 | 63.00 |
| | | ENTRO CLOACE (23355) | | 4.00 | 32.00 | 63.00 |
| | | KLEB. PN. (13883) | | XX | 63.00 | 32.00 |
| | | SALMONELLA TYPH. (14028) | | 16.00 | 63.00 | 125.00 |
| | GRAM POSITIVE BACTERIA | STAPH AUREUS (25923) | | 63.00 | 63.00 | 32.00 |
| | | STAPH. EPI (12228) | | 4.00 | 4.00 | 4.00 |
| | | STREP. PYR. (19615) | | 4.00 | 8.00 | 16.00 |
| | YEASTS | SAC. CERV. | | 125.00 | 188.00 | 94.00 |
| | | PICHIA | | 32.00 | 188.00 | 94.00 |
| | | | | | | |
| | | | | | | |
| | | | | | | |
| | | TABLE II | | | | |

| SEQUENCE I.D. | ENDGROUP (N TERMINUS) | | | | | | | | | | | | | ENDGROUP (C TERMINUS) | |
|---|---|---|---|---|---|---|---|---|---|---|---|---|---|---|---|
| 1 | (H-) | L | V | L | K | L | M | K | Y | K | L | K | G | L | (AMIDE-) | COL-1 |
| 2 | (H-) | L | L | L | K | L | L | K | N | P | L | K | I | G | V | (AMIDE-) | COL-2 |
| 3 | (H-) | L | L | L | K | L | L | K | L | M | N | L | K | L | G | H | Y | (AMIDE-) | COL-3 |
| 4 | (H-) | | | K | K | I | K | E | K | Y | D | K | M | K | | | (AMIDE-) | |

TABLE I

FIG. 1

| ANTIMICROBIAL DATA | ORGANISM (ATCC) | SEQ. ID | 1 | 2 | 3 |
|---|---|---|---|---|---|
| GRAM NEGATIVE BACTERIA | E. COLI (25922) | | 16.00 | 32.00 | 8.00 |
| | PS. ARUGINOSA (13883) | | 8.00 | 125.00 | 63.00 |
| | ENTRO CLOACE (23355) | | 4.00 | 32.00 | 63.00 |
| | KLEB. PN. (13883) | | XX | | |
| | SALMONELLA TYPH. (14028) | | 16.00 | 63.00 | 32.00 |
| GRAM POSITIVE BACTERIA | STAPH AUREUS (25923) | | 63.00 | 63.00 | 125.00 |
| | STAPH. EPI (12228) | | 4.00 | 4.00 | 32.00 |
| | STREP. PYR. (19615) | | 4.00 | 8.00 | 4.00 |
| YEASTS | SAC. CERV. | | 125.00 | 188.00 | 16.00 |
| | PICHIA | | 32.00 | 188.00 | 94.00 |
| | | | | | 94.00 |
| TABLE II | | | | | |

FIG. 2

| SEQ. I.D. | MOLEC. WEIGHT | SOLUBILITY (ug/100g) | BIOSTABILITY MAMMALIAN | HALF-LIFE YEAST | (HOURS) E. COLI |
|---|---|---|---|---|---|
| 1 | 2325.09 | 69.97 | 5.50 | 0.50 | 0.03 |
| 2 | 2268.03 | 59.40 | 5.50 | 0.50 | 0.03 |
| 3 | 2375.12 | 44.18 | 5.50 | 0.50 | 0.03 |
| 4 | 1548.93 | 70.46 | 1.30 | 0.05 | 0.03 |

TABLE III

FIG. 3

| SEQ. ID NO.: | MW | ISOELECTRIC CHARGE AT PH7 | 1 mg=nM | % CHARGED | % ACIDIC | % BASIC | % POLAR | % HYDROPHOBIC | % ALPHA | % BETA | % TURN |
|---|---|---|---|---|---|---|---|---|---|---|---|
| 1 | 2325.09 | 10.56 | 7.90 | 426.00 | 45.00 | 0.00 | 40.00 | 5.00 | 40.00 | 100.00 | 0.00 | 0.00 |
| 2 | 2268.03 | 10.70 | 5.90 | 437.00 | 30.00 | 0.00 | 30.00 | 5.00 | 55.00 | 80.00 | 20.00 | 0.00 |
| 3 | 2375.12 | 10.32 | 5.07 | 417.00 | 35.00 | 0.00 | 25.00 | 10.00 | 50.00 | 100.00 | 0.00 | 0.00 |
| 4 | 1548.93 | 10.01 | 4.90 | 638.00 | 83.33 | 16.67 | 58.33 | 8.33 | 8.33 | 100.00 | 0.00 | 0.00 |

TABLE IV

FIG. 4

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 20 Amino Acids
       (B) TYPE: Amino Acid
       (D) TOPOLOGY: UNKNOWN (ii) MOLECULE TYPE: Peptide (xi) SEQUENCE DESCRIPTION: SEQ ID NO: 1:

```
Leu Val Leu Leu Lys Lys Leu Met Lys Lys
1               5                   10
Tyr Lys Lys Leu Lys Lys Leu Gly Gly Leu
                15                  20
```

(2) INFORMATION FOR SEQ ID NO: 2:

(i) SEQUENCE CHARACTERISTICS:
       (A) LENGTH: 20 Amino Acids
       (B) TYPE: Amino Acid
       (D) TOPOLOGY: UNKNOWN (ii) MOLECULE TYPE: Peptide (xi) SEQUENCE DESCRIPTION: SEQ ID NO: 2:

```
Leu Leu Leu Leu Lys Leu Leu Leu Lys Lys
1               5                   10
Asn Pro Lys Leu Lys Lys Leu Ile Gly Val
                15                  20
```

(2) INFORMATION FOR SEQ ID NO: 3:

(i) SEQUENCE CHARACTERISTICS:
       (A) LENGTH: 20 Amino Acids
       (B) TYPE: Amino Acid
       (D) TOPOLOGY: UNKNOWN (ii) MOLECULE TYPE: Peptide (xi) SEQUENCE DESCRIPTION: SEQ ID NO: 3:

```
Leu Leu Leu Leu Lys Lys Leu Leu Lys Leu
1               5                   10
Met Asn Leu Leu Lys Lys Leu Gly His Tyr
                15                  20
```

(2) INFORMATION FOR SEQ ID NO: 4:

(i) SEQUENCE CHARACTERISTICS:
       (A) LENGTH: 12 Amino Acids
       (B) TYPE: Amino Acid
       (D) TOPOLOGY: UNKNOWN (ii) MOLECULE TYPE: Peptide (xi) SEQUENCE DESCRIPTION: SEQ ID NO: 4:

```
Lys Lys Ile Lys Glu Lys Tyr Asp Lys Met
1               5                   10
Lys Lys
```

YEAST-TOXIN-RELATED PROTEIN FOR ANTIMICROBIAL VACCINE AND STERILIZING PRESERVATIVE USE

FIELD OF THE INVENTION

A new class of broad spectrum antimicrobials has been identified with molecular weight below 2600, high aqueous solubility, low cytotoxicity to mammalian cells such as human erythrocytes and usefulness as preservatives, antibacterial, antifungal and food additive applications.

BACKGROUND OF THE INVENTION

The present invention describes pharmaceutically relevant compounds for use as preservatives and antimicrobial application and may be applied to treatment or prevention of manifestations of infectious disease. More specifically, the present invention includes a new class of polypeptides and their associated salts thereof, which possess broad spectrum antimicrobial potency and favorable therapeutic profiles. In addition, the application may embody a variety of chemical disinfectant uses for reduction in bacterial growth and sterilization. Applications are widespread, from antibacterial and antifungal creams, food preservatives, indwelling medical device coatings to antibiotics for human disease treatment. Polypeptides are key carriers of biochemical information in all mammalian systems, thus garnering considerable interest as therapeutic and diagnostic reagents. No such polypeptide sequences as described in the present invention have been previously discovered or isolated either synthetically using de novo design or purified from compositions in the natural ecosystems.

SUMMARY OF INVENTION

An object of the invention is to provide a novel family of antimicrobial and preservative compounds isolated and derivatized from microbial toxin related molecules, specifically the Kluyveromyces lactis killer toxin family of precursors, receptors and proteins.

Certain yeast strains have been found to produce a novel toxin with a power to kill pathogenic organisms. Presence of double stranded linear plasmids have been shown to be the genetic basis for killer toxin production. The search for such a novel killer toxin have been done in linear double stranded plasmid containing the yeast, Kluveromyces lactis. For example, toxin-producing colonies of *K. lactis* growing on a lawn of sensitive *S. cerevisiae* produce disks of inhibited growth. The present invention addresses the ability to produce toxin and the effects of this toxin on pathogenic organism like *PSeudomonas aeroginosa, Staph. epidermis* and *Candida albicans*.

The *K. lactis* toxin is a 155 kDa protein of three nonidentical subunits which is active against *S. cerevisiae*. The 1146 amino acids which make up the alpha and beta unit of the *K. lactis* toxin is composed of three subunits: alpha (amino acid 30–892), beta (895–1146) and gamma, and belongs to the family of glycosyl hydrolases and chitin binding proteins. The alpha subunit is a potent exochitinase. Along with the beta subunit, it plays a role in the initial interaction of the toxin with sensitive cells and allows the active toxin, the gamma subunit, to gain entry into the cell. In this way, the alpha and beta subunits are membrane active and therefore can serve as potent antimicrobial peptides for lysing selectively various competing or pathogenic bacteria and fungi. An essential chitinase activity of the alpha subunit is required for interaction with sensitive cells. However, the gamma subunit is responsible for the major effect of the toxin, a block in the G1 phase of the cell cycle at the event after which cells are committed to DNA synthesis and cell division.

Study of microbial toxins serves as an example of a general approach to structure-based vaccine and chemical design. These toxins exhibit a remarkable ability to stimulate the mucosal immune system, and this property can be maintained by engineered fusion proteins based on the native toxin structure. That is, the modified toxin can continue to evoke a strong mucosal immune response, and this response can be directed against an epitope conformation characteristic of the original pathogen. U.S. Pat. No. 5336492, Bacillus thuringiensis isolates denoted B.T. PS81F, active against lepidopteran pests (Payne, et al. 1994) teaches a novel Bacillus thuringiensis (B.t.) toxin gene toxic to lepidopteran insects, and the method by which DNA encoding the B.t. toxin can be used to transform various prokaryotic and eukaryotic microbes to express the B.t. toxin. These recombinant microbes can be used to control lepidopteran insects in various environments. The present invention provides an appropriate antimicrobial peptide to incorporate these selected epitopes from foreign pathogens into the native framework of the toxin such that crucial features of both the epitope and the toxin are maintained.

More specifically, the compounds (SEQ. I.D. 1–3) are related by a small fragment of a much larger yeast killer toxin-related proteins expressed in yeasts (beta subunit precursor protein, sequence fragment 1026–1037, *K. lactis*) as listed by amino acid in (SEQ. I.D. 4). With this background, SEQ. 1–3 corresponds to modifications to the partial amino acid fragment built around the K-KK motif common to the beta subunit yeast killer toxin precursor proteins which assist membrane entry of the actual yeast toxic gamma subunit. It is known that microbial toxins generally and yeast killer toxic domains specifically are important regulators of microbial competition, in particular in membrane disruption and chitin synthesis. The usefulness of peptide animicrobials have considerable promise for controlling topical infections related to abnormal cell proliferation and microbial infection. Identifying antimicrobial activity in yeast killer toxin related proteins is therefore a significant step toward understanding how to control pathogenic infection and cell growth.

It is further an object of the present invention to provide a novel class of antimicrobials which inhibit growth or otherwise act microcidally in infections related to gram negative and positive bacteria, protozoa and/or parasites, fungi and the like. The minimum inhibitory concentration (MIC ug/mL) of the compounds indicate both broad spectrum and highly targeted microcidal potency.

Advantages of such compounds and other objects of invention will be apparent to those skilled in the art, as outlined in the Detailed Description of the Invention.

DETAILED DESCRIPTION OF THE INVENTION.

The polypeptides discovered and described herein comprise a novel class of preservative and antimicrobial having a molecular weight less than 2600, aqueous solubility at neutral pH of approximately 100 times or more than their 50% inhibitory concentration, and non-cytotoxicity in various physiological media and sera, including membrane stability for mammalian red blood cells.

Once specified as an amino acid sequence and its derivatized salts or fluorogenic chemicals, these compounds can be readily synthesized using techniques and chemical steps known to the art, such as commercially standard solid phase synthesis, solution phase synthesis, and peptides stepwise sequenced onto, for example, a polyethylene or similarly coated bead, bandage, patch or prosthetic device. In accordance with the present invention, the antimicrobial peptides may be prepared by, for example, a first method, i.e. solid phase method employing an Fmoc amino acid (Sheppard, R. C. et al. J. Chem. Soc. Chem. Comm. 165–166, 1985). The second method for synthesizing the antimicrobial peptides of the present invention is a solid phase method employing the Boc-amino acid according to Merrifield, J. Am. Chem. Soc., 85, 2149, 1963. The solid phase syntheses of peptides have commercialized the availability of large-scale (numbering several hundred thousands) peptide production. The success of these developments largely depended on the elimination of intermediates in the synthesis and substitution of a platform or solid support to attach each amino acid to; the resulting short peptide chains can be manufactured using resin beads, cotton, or plastic pins. Besides the above mentioned methods of producing the peptides, the peptides may also be produced by other conventional chemical synthetic methods, methods of producing a DNA correspond to the desired peptide and introducing the DNA into a suitable vector for production in animal cells or microorganisms to produce the desired peptides, or methods of chemically modifying the produced peptide in a suitable manner. These amino acid constituents can consist of L- or D- enantiomeric derivatives and modified petide backbones such as peptoids and mimetics. Further since the relevant compounds derive from similar naturally occurring amino acid sequences, aqueous or lipophilic (e.g. octanol or acetone) isolation and purification can likewise support manufacture and pharmaceutical supply.

The amino acids (SEQ. I.D. No. 1–4) shown in Table I identify essential fragments to demonstrate preservative or antimicrobial efficacy, but are not limited by truncated or synthetic amino acid sequences which share at least in part or in whole the amino acid sequence shown in Tables I and II. Various analogs and derivatives can be predicted by those skilled in the art of peptide chemistry and computer modelling, but within the scope of the disclosure may be equivalent in biological function and structure. Examples of such derivatives are presented in Tables I–III. To manipulate the polypeptide sequence, standard methods including probing the importance of each amino acid by sequential alanine or glycine substitutions, examining sterically restricted cis- and trans-substitutions with the aromatic proline, and progressively shortening the amino (N-) terminus until antimicrobial potency diminishes quantitatively.

Table II shows the spectrum of preservative and antimicrobial effectiveness for synthetic peptides of the present invention against representative organisms and corresponding infectious ailments. Table III lists the minimum inhibitory concentration (ug/mL) for the various organisms assayed in Mueller-Hinton growth media. Details of the microbiological techniques employed are available to those skilled in the art, for instance from the American Type Tissue Culture Catalog (ATCC, Md.) or DIFCO Manual, 10th Edition, 1984, pp. 78–80. For instance, a cultured solution of the bacterial strains Escherichia coli (American Tissue Culture Collection, MD) ATCC 259222 and Pseudomonas aeruginosa ATCC 27853 can be tested to model Gram-negative bacteria. Bacteria were grown overnight at 37 C in Mueller-Hinton broth, reinoculated and incubated at 37 C to reach the exponential phase of bacterial growth [i.e. a final bacterial suspension cantaining from 100,000 to 500,000 colony-forming units (CFU)/mL]. In 96 well tissue culture plates, peptides dissolved in distilled water were added to the bacterial suspension at concentrations varying between 1000 to 2 ug/mL derived from serial dilutions, and then incubated overnight at 37 C. The 50% inhibitory concentration and minimum inhibitory concentration (MIC) were defined as the concentration of peptide at which there was 50% reduction in the optical density (absorbance, OD) and the concentration at which there was no change in optical density, between time 0 and 16 h at 620 nm using a multiscan plate reader.

Table III lists the approximate pharmacokinetics of synthetic peptides described in the present invention which solubilize readily, persist in conformationally active secondary structures in vivo, and induce lysis of representative bacteria, yeast and fungi. These determinations derive from optical density readings (O.D.) and rely on spectrophotometric absorbance from known initial concentrations as reference standards. It is worth noting that although the peptide antimicrobials show 30+% homology with the yeast killer toxin beta subunit fragment, they have very favorable safety profiles on mammalian cells. For example, when human red blood cells are exposed in whole blood to SEQ. 1, at a peptide concentration of 63 ug/mL, no hemolysis is detectable following centrifugation and spectrophotometric analysis for extracellular hemoglobin. Perhaps, as significant, the safety profile derives from very specific amino acid substitutions, since substitution for less than 20% of the amino acids in SEQ. 1 renders SEQ. 2 hemolytic to 20% at 63 ug/mL and 35% substitution in SEQ. 1 renders SEQ. 3 hemolytic to 100%. Therefore, sequence identity and variation translate directly to the functional balance between microbial inhibition and mammalian safety. The optimal therapeutic index for dosage and effective antimicrobial inhibition of a particular polypeptide or salt thereof follow routinely without elaborate laboratory determinations by those skilled in the art of pharmacokinetics and metabolic pathways using, for instance, various cytochrome and liver enzymes in vivo.

One clear conclusion from tabulated data is that the polypeptides of the present invention display a broad spectrum of preservative and antimicrobial effectiveness, including favorable therapeutic indices as well as microcidal effects against gram positive and gram negative bacteria, strains of yeast and fungi and the like. In physiological or nutritional media, these antibiotic properties offer further sterilizing or preservative use for combining such antimicrobial action with other therapeutics in synergistic formulations.

To those skilled in the art of pharmaceutical formulation, the present invention serves as an active ingredient concentrated to deliver relief of clinical ailments using a generally regarded as safe (GRAS) carrier prepared using the results herein. This carrier comprises fillers, non-toxic buffers, physiological (phosphate buffered) saline, and various adjustable viscous creams or ointments (e.g. methyl cellulose thickeners). Acidic pH adjustment for physiological application further comprises addition of regulatory acids, bases and buffers, such as citric or acetic acid generally formulated but not limited to give a lower pH than neutral for peptide stability and lengthened half-lives. Suitable lyophilized powders, liquids, or semi-solid forms include injectable compositions via catheter or syringe, oral tables or capsules, pastes, gums, ointments, patches and inhalable constituents. Co-administration of the described polypeptides can further be combined with proteinase inhibitors (such as trypsin or chymotrypsin inhibitors) and synergistic formulations designed to enhance the inhibitory potency of the present invention.

These detailed descriptions are understood as illustrative and subject to modification or change by those skilled in the art, thereby included within the purview and spirit of the appended claims.

SUMMARY OF THE ANTIMICROBIAL AMINO ACID SEQUENCE DATA

An object of this invention is to provide a short amino acid chain capable of inhibiting microbial growth and spoilage of an aqueous solution containing whole cells, membranes, and in vivo infectious agents. Novel antimicrobial peptides are descibed herein. The peptides comprise amino acid chains represented by the following single letter designations:

LVLLKKLMKKYKKLKKLGGL as represented in ID sequence No.1

LLLLKLLLKKNPKLKKLIGV as represented in ID sequence No.2

LLLLKKLLKLMNLLKKLGHY as represented in ID sequence No.3

KKIKEKYDKMKK as represented in ID sequence No.4

Definitions

The single-letter amino acid representation is used (i.e A=alanine; C=cysteine, D=aspartic acid; E=glutamic acid; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; Y=tyrosine).

The amino acid sequences of the present invention are also identified herein by their three letter amino acid representations. The convention for three-letter amino acid representations is as follows: Ala=alanine; Cys=cysteine; Asp=aspartic acid; Glu=glutamic acid; Phe=phenylalanine; Gly=glycine; His=histidine; Ile=isoleucine; Lys=lysine; Leu=leucine; Met=methionine; Asn=asparagine; Pro=proline; Gln=glutamine; Arg=arginine; Ser=serine; Thr=threonine; Val=valine; Trp=tryptophan; Tyr=tyrosine.

BRIEF DESCRIPTION OF THE DRAWINGS

FIG. 1 shows the primary sequence of the novel peptides.

FIG. 2 shows certain antimicrobial properties of the novel peptides.

FIG. 3 shows the comparative in vivo pharmacokinetic properties of the novel peptides against infectious organisms.

FIG. 4 shows the secondary structure of the novel peptides.

DETAILED DESCRIPTION OF THE ANTIMICROBIAL CHEMICAL INNOVATIONS

In accordance with the present invention, there is provided a peptide having antimicrobial activity, the peptide consisting of an amino acid chain represented by:

```
Leu Val Leu Leu Lys Lys Leu Met Lys Lys
1               5                   10

Tyr Lys Lys Leu Lys Lys Leu Gly Gly Leu
                15                  20
as set forth in SEQ. ID. No. 1, or salts thereof;

Leu Leu Leu Leu Lys Leu Leu Leu Lys Lys
1               5                   10

Asn Pro Lys Leu Lys Lys Leu Ile Gly Val
                15                  20
as set forth in SEQ. ID. No. 2, or salts thereof;

Leu Leu Leu Leu Lys Lys Leu Leu Lys Leu
1               5                   10

Met Asn Leu Leu Lys Lys Leu Gly His Tyr
                15                  20
as set forth in SEQ. ID. No. 3, or salts thereof;

Lys Lys Ile Lys Glu Lys Tyr Asp Lys Met
1               5                   10

Lys Lys
                15                  20
as set forth in SEQ. ID. No. 4, or salts thereof;
```

Secondary Structure Determination

The antimicrobial peptides (1–4) according to the present invention were subjected to a prediction method for determining their secondary structure as an alpha-helical or beta-sheet configuration using the Garnier-Robson and Chou-Fasman criteria (e.g. Chou, Biopolymers, 33:1405, 1993). This analysis as shown in Table IV revealed a predominantly alpha-helical structure in (SEQ. I.D. 1–4) with an approximate 5.4 angstrom per turn distance between residues.

A number of structural advantages feature in SEQ. 1–3 in addition to the primary function of no longer requiring either long peptide manufacturing and three subunit antimicrobial action of the yeast killer toxin precursor. Oral formulations generally depend on bioavailability in vivo which is often a function of molecular weight. The mammalian in vivo half-life (hours) for SEQ. 1–3, for example, is 4 times longer than the yeast killer toxin precursor fragment SEQ 4. Furthermore, the elimination of Asp- amino acids in the precursor fragment SEQ. 4, which alone lacks antimicrobial action, renders SEQ. 1–3 resistant to basic or neutral pH deamidation reactions which modify peptides structurally by chemical reaction or hydrolysis. The elimination of Met- amino acids in the precursor protein, SEQ. 3, which alone lacks antimicrobial action, renders SEQ. 2 resistant to oxidation reactions in air and photoactive oxidation which modify peptides structurally by chemical reaction. It is clear that the fundamental peptide chemistry of SEQ. 1–3 renders improved stability to side-reactions for improved bioavailability while providing sub-micromolar antimicrobial potency.

The arrangement of these residues provides a largely hydrophilic region alternating with hydrophobic residues substantially on the surface of the cell membrane. The action of alpha-helical peptides, in particular, derives from their natural proclivity for forming such ion channels across membrane bilayers, particularly for those peptides longer than 20 residues. Ion channels formed by shorter (8–12 residue) monomers span the membrane bilayer as head-to-tail dimers or larger self-aggregated units. For favorable ion channel formation the aggregated confirmation places the hydrophilic residues inward and the hydrophobic residues free to interact with the cell wall's phospholipid groups. To induce potent antibacterial activity, the ion channel therefore serves to neutralize the membrane potential, thus ceasing normal charge transfer. This mechanism differs from bacteriostatic chemicals which for example, inhibit protein or DNA synthesis and offers advantages for bacteriocidal applications where contact killing is important. The antimicrobial effect may also be augmented by modifying the side chain of a suitable amino acid residue or by replacing a specific amino acid residue by another amino acid.

What is claimed is:

1. A polypeptide containing:

```
Leu Val Leu Leu Lys Lys Leu Met Lys Lys
1               5                   10
Tyr Lys Lys Leu Lys Lys Leu Gly Gly Leu
                15                  20
``` as set forth in SEQ. ID. No. 1, or salts thereof.

2. A polypeptide containing:

```
Leu Leu Leu Leu Lys Leu Leu Leu Lys Lys
1               5                   10
Asn Pro Lys Leu Lys Lys Leu Ile Gly Val
                15                  20
``` as set forth in SEQ. ID. No. 2, or salts thereof.

3. A polypeptide containing:

```
Leu Leu Leu Leu Lys Lys Leu Leu Lys Leu
1               5                   10
Met Asn Leu Leu Lys Lys Leu Gly His Tyr
                15                  20
``` as set forth in SEQ. ID. No. 3, or salts thereof.

4. A polypeptide containing:

```
Lys Lys Ile Lys Glu Lys Tyr Asp Lys Met
1               5                   10
Lys Lys
``` as set forth in SEQ. ID. No. 4, or salts thereof wherein the polypeptide has a molecular weight below 2600 g/mole.

* * * * *